United States Patent
Caprasse et al.

(10) Patent No.: US 7,482,419 B2
(45) Date of Patent: Jan. 27, 2009

(54) SILSESQUIOXANE RESIN WAX

(75) Inventors: Virginie Caprasse, Oreye (BE); Timothy Gregg Hueston, Midland, MI (US); Tina Marie Leaym, Saginaw, MI (US); Virginia Kay O'Neil, Midland, MI (US); Lori Ann Stark-Kasley, Midland, MI (US); Isabelle Van Reeth, Incourt (BE)

(73) Assignee: Dow Corning Corporation, Midland, MI (US)

( * ) Notice: Subject to any disclaimer, the term of this patent is extended or adjusted under 35 U.S.C. 154(b) by 44 days.

(21) Appl. No.: 10/591,187

(22) PCT Filed: Apr. 5, 2005

(86) PCT No.: PCT/US2005/011705

§ 371 (c)(1), (2), (4) Date: Aug. 30, 2006

(87) PCT Pub. No.: WO2005/100444

PCT Pub. Date: Oct. 27, 2005

(65) Prior Publication Data

US 2007/0149703 A1 Jun. 28, 2007

Related U.S. Application Data

(60) Provisional application No. 60/561,623, filed on Apr. 12, 2004.

(51) Int. Cl.
*C08G 77/08* (2006.01)

(52) U.S. Cl. .............................. 528/15; 528/31; 528/39

(58) Field of Classification Search .................. 528/31, 528/39, 15
See application file for complete search history.

(56) References Cited

U.S. PATENT DOCUMENTS

| | | | |
|---|---|---|---|
| 3,609,178 A * | 9/1971 | Thomas | 528/34 |
| 5,684,112 A * | 11/1997 | Berthiaume et al. | 528/29 |
| 5,733,537 A | 3/1998 | Halloran et al. | |
| 5,932,231 A | 8/1999 | LeGrow et al. | |
| 6,071,503 A | 6/2000 | Drechsler et al. | |
| 6,139,823 A | 10/2000 | Drechsler et al. | |
| 6,184,260 B1 * | 2/2001 | Zhong | 521/77 |
| 6,200,554 B1 * | 3/2001 | Yeoh et al. | 424/70.12 |
| 6,270,561 B1 | 8/2001 | Nguyen | |
| 6,340,466 B1 | 1/2002 | Drechsler et al. | |
| 6,376,635 B1 * | 4/2002 | Amako et al. | 528/31 |
| 6,596,404 B1 * | 7/2003 | Albaugh et al. | 428/447 |
| 2002/0064509 A1 | 5/2002 | Grimm et al. | |
| 2002/0120036 A1 | 8/2002 | Pinzon et al. | |
| 2003/0082218 A1 | 5/2003 | Ichinohe et al. | |
| 2003/0086888 A1 | 5/2003 | LeGrow et al. | |
| 2003/0125427 A9 | 7/2003 | Pinzon et al. | |
| 2003/0147837 A1 | 8/2003 | Cavazzuti et al. | |
| 2003/0185780 A1 | 10/2003 | Ferrari et al. | |
| 2004/0028636 A1 | 2/2004 | Collin | |

FOREIGN PATENT DOCUMENTS

| | | |
|---|---|---|
| EP | 1314415 | 5/2003 |
| WO | WO97/17058 | 5/1997 |
| WO | WO97/17059 | 5/1997 |
| WO | WO02/47608 | 6/2002 |
| WO | WO02/47619 | 6/2002 |
| WO | WO02/47623 | 6/2002 |
| WO | WO02/47624 | 6/2002 |
| WO | WO02/47657 | 6/2002 |
| WO | WO02/058643 | 8/2002 |

* cited by examiner

*Primary Examiner*—Margaret G Moore
(74) *Attorney, Agent, or Firm*—Patricia M. Scaduto

(57) ABSTRACT

A silsesquioxane resin wax composition, method for its preparation, and use in personal, household, automotive and medical care compositions are disclosed. The silsesquioxane resin wax can also find utility in a variety of oil and gas field applications, such as for crude oil wax control.

13 Claims, No Drawings

SILSESQUIOXANE RESIN WAX

CROSS REFERENCE TO RELATED APPLICATIONS

This application is a U.S. national stage filing under 35 U.S.C. §371 of PCT Application No. PCT/US2005/11705 filed on 5 Apr. 2005 currently pending, which claims the benefit of U.S. Provisional Patent Application No. 60/561,623 filed 12 Apr. 2004 under 35 U.S.C. §119(e). PCT Application No. PCT/US2005/011705 and U.S. Provisional Patent Application No. 60/561,623 are hereby incorporated by reference.

FIELD OF THE INVENTION

The present invention relates to a silsesquioxane resin wax composition, methods for its preparation, and uses in personal, household, automotive and medical care compositions. The silsesquioxane resin wax can also be used in a variety of oil and gas field applications, such as for crude oil wax control.

BACKGROUND OF THE INVENTION

Siloxane resins of the general formula $R_nSiO_{(4-n)/2}$, where R is an alkyl group and n is generally less than 1.8, are an important family of silicone polymers because of their utility in many commercial applications such as adhesive compositions and coatings applications. One particular subclass of siloxane resins, known as MQ resins (since they comprise primarily of "M" units of the general formula $R_3SiO_{1/2}$ and "Q" units of the general formula $SiO_2$), have found utility in cosmetic formulations. In particular MQ resins are commonly used in "extended wear" or "transfer resistant" cosmetic formulations. In these formulations, MQ resins enhance the substantivity of the pigments or other formulation actives to skin after application creating a longer lasting, and hence extended wear product.

Representative examples of transfer resistant cosmetic compositions using MQ resins are found in U.S. Pat. Nos. 6,071,503, 6,074,654, 6,139,823, 6,340,466, WO 97/17058, and WO 97/17059 which disclose compositions comprising the combination of organosiloxane resins and fluid diorganosiloxane resins with a volatile carrier.

Silsesquioxane resins of the general formula $RSiO_{3/2}$ have also been used as additives in personal care formulations for a variety of functions. For example, in U.S. Pat. No. 5,733,537 by Halloran teaches the use of a non-polar silsesquioxane resin as a hair fixative. U.S. Patent application publication 20030086888 by Legrow discloses trimethylsilyalkylsilsesquioxanes in leave-on compositions for personal care. More recently, U.S. provisional application 60/514,001 and 60/541,002, as filed by the same assignee as the present application, discloses MQ-propyl resins compositions and use in a variety of personal care formulations. Also, U.S. provisional application 60/553,450, as filed by the same assignee as the present application, discloses alkyl-phenyl silsesquioxane resins in a variety of personal care applications.

While these references represent advances in the art, there is still a need for improved siloxane resins for use in skin care formulations that offer extended durability to cosmetic formulations, but also provide other functional benefits, such as moisturization, occlusivity, and improved feel. Furthermore, there is a need for siloxane resins having wax like characteristics, but yet still possess solubility in commonly used personal care solvents, including volatile silicones The present inventors have discovered improved siloxane resins by incorporating two distinct hydrocarbon groups in a silsesquioxane resin. The first hydrocarbon has 1 to 8 carbon atoms, and the second hydrocarbon group has 9-40 carbon atoms. The resulting siloxane resins, herein referred to as silsesquioxane resin wax, improve the durability and substantivity of cosmetics after topical application to skin, improved the non transfer of color cosmetic formulations such as castor oil based lipsticks and have improved compatibility over other silicone waxes in cosmetic ingredients and fragrances while also providing other functional benefits such as moisturization, occlusivity, and improved feel. These silsesquioxane resin waxes can also act as texture and rheology modifiers in water-in-oil and oil-in-water emulsions. The melting points and overall hydrocarbon content of the silsesquioxane resins can be adjusted to provide varying aesthetic benefits from a personal care formulation. The silsesquioxane resin wax can also be used in personal care formulations to improve fragrance retention and delivery of actives.

SUMMARY OF THE INVENTION

The present invention relates to a silsesquioxane resin wax comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R' is a monovalent hydrocarbon having 9-40 carbon atoms, R" is a monovalent hydrocarbon group having 1 to 8 carbon atoms, an aryl group.

The compositions of the present invention can be incorporated into a variety of personal, household, automotive or medical care compositions. The silsesquioxane resin wax enhances the durability and substantivity of cosmetics on skin after topical application from a formulation comprising the composition of the present invention. The silsesquioxane resin wax can also be used for crude wax control in oil and gas operations.

DETAILED DESCRIPTION OF THE INVENTION

The present invention relates to a silsesquioxane resin wax comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R' is a monovalent hydrocarbon having 9-40 carbon atoms, R" is a monovalent hydrocarbon group having 1 to 8 carbon atoms or an aryl group. As used herein, x and y represent the mole fraction of $(R_2R'SiO_{1/2})$ and $(R''SiO_{3/2})$ siloxy units relative to each other present in the silsesquioxane resin wax. This, the mole fraction of $(R_2R'SiO_{1/2})$ and $(R''SiO_{3/2})$ siloxy units each can independently vary from 0.05 to 0.95. Typically, the value of x is 0.05 to 0.95, or alternatively, 0.2 to 0.8, the value of y is 0.05 to 0.95, alternatively 0.2 to 0.8. However, the combination of $(R_2R'SiO_{1/2})$ and $(R''SiO_{3/2})$ siloxy units present must total at least 40 mole %, alternatively 60 mole %, or alternatively 90 mole % of all siloxy units present in the silsesquioxane resin wax. The silsesquioxane resin wax may be a liquid, soft solid, or solid material at room temperature.

The silsesquioxane resin wax can contain additional siloxy units such as (i) $(R^1_3SiO_{1/2})_a$, (ii) $(R^2_2SiO_{2/2})_b$, (iii) $(R^3SiO_{3/2})_c$, or (iv) $(SiO_{4/2})_d$ units which are commonly known in the art, and also used herein, as M, D, T, and Q units respectively. The amount of each unit present in the silsesquioxane resin wax can be expressed as a mole fraction of the total number of moles of all siloxy units present in the silsesquioxane resin wax. Thus, the silsesquioxane resin wax of the present invention comprise the units:

(i) $(R^1{}_3SiO_{1/2})_a$
(ii) $(R^2{}_2SiO_{2/2})_b$
(iii) $(R^3SiO_{3/2})_c$,
(iv) $(SiO_{4/2})_d$,
(v) $(R_2R'SiO_{1/2})_x$ and
(vi) $(R''SiO_{3/2})_y$, wherein R, $R^1$, $R^2$, and $R^3$ are independently an alkyl group having from 1 to 8 carbon atoms, an aryl group, a carbinol group, or an amino group, R' is a monovalent hydrocarbon having 9-40 carbon atoms, R'' is a monovalent hydrocarbon group having 1 to 8 carbon atoms, a, b, c, and d have value of zero to 0.6, x and y have a value of 0.05 to 0.95, with the provisos that the value of x+y is equal to or greater than 0.40, and the value of a+b+c+d+x+y=1.

R' can be any linear or branched monovalent hydrocarbon having 9 to 40 carbons. Alternatively, R' is a C18-C40 hydrocarbon group. R'' can be a methyl, ethyl, propyl, butyl, pentyl, hexyl, heptyl, octyl, or aryl group. Alternatively, R'' is propyl.

In one embodiment of the present invention, the selection of R' and the ratio of y/x is selected such that the silsesquioxane resin wax has a melting point greater than 30° C.

The R, $R^1$, $R^2$, and $R^3$ in the units of the silsesquioxane resin wax are independently an alkyl group having from 1 to 8 carbon atoms, an aryl group, a carbinol group, an amino group, or a quaternary ammonium group. The alkyl groups are illustrated by methyl, ethyl, propyl, butyl, pentyl, hexyl, and octyl. The aryl groups are illustrated by phenyl, naphthyl, benzyl, tolyl, xylyl, xenyl, methylphenyl, 2-phenylethyl, 2-phenylpropyl (α-methylstyrene) 2-phenyl-2-methylethyl, chlorophenyl, bromophenyl and fluorophenyl with the aryl group typically being phenyl.

For the purposes of this invention a "carbinol group" is defined as any group containing at least one carbon-bonded hydroxyl (COH) radical. Thus the carbinol groups may contain more than one COH radical such as for example

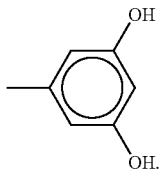

The carbinol group if free of aryl groups has at least 3 carbon atoms, or an aryl-containing carbinol group having at least 6 carbon atoms. The carbinol group free of aryl groups having at least 3 carbon atoms is illustrated by groups having the formula $R^4OH$ wherein $R^4$ is a divalent hydrocarbon radical having at least 3 carbon atoms or divalent hydrocarbonoxy radical having at least 3 carbon atoms. The group $R^4$ is illustrated by alkylene radicals such as —$(CH_2)_x$— where x has a value of 3 to 10, —$CH_2CH(CH_3)$—, —$CH_2CH(CH_3)CH_2$—, —$CH_2CH_2CH(CH_2CH_3)CH_2CH_2CH_2$—, and —$OCH(CH_3)(CH_2)_x$— wherein x has a value of 1 to 10.

The aryl-containing carbinol group having at least 6 carbon atoms is illustrated by groups having the formula $R^5OH$ wherein $R^5$ is an arylene radical such as —$(CH_2)_xC_6H_4$— wherein x has a value of 0 to 10, —$CH_2CH(CH_3)(CH_2)_xC_6H_4$— wherein x has a value of 0 to 10, —$(CH_2)_xC_6H_4(CH_2)_x$— wherein x has a value of 1 to 10. The aryl-containing carbinol groups typically have from 6 to 14 atoms.

The amino group is illustrated by groups having the formula —$R^6NH_2$ or —$R^6NHR^7NH_2$ wherein $R^6$ is a divalent hydrocarbon radical having at least 2 carbon atoms and $R^7$ is a divalent hydrocarbon radical having at least 2 carbon atoms. The group $R^6$ is typically an alkylene radical having from 2 to 20 carbon atoms. $R^6$ is illustrated by ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene.

$R^7$ is typically an alkylene radical having from 2 to 20 carbon atoms. $R^7$ is illustrated by ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene.

Typical amino groups are —$CH_2CH_2CH_2NH_2$ and —$CH_2(CH_3)CHCH_2(H)NCH_3$, —$CH_2CH_2NHCH_2CH_2NH_2$, —$CH_2CH_2NH_2$, —$CH_2CH_2NHCH_3$, —$CH_2CH_2CH_2CH_2NH_2$, —$(CH_2CH_2NH)_3H$, and —$CH_2CH_2NHCH_2CH_2NHC_4H_9$.

Typically, R is a methyl group, $R^1$ is a methyl group, $R^2$ is a methyl or phenyl group, and $R^3$ is a methyl group.

Any individual D, T or Q siloxane units of the silsesquioxane resin wax can also contain a hydroxy group and/or alkoxy group. Such siloxane units containing hydroxy and/or alkoxy groups are commonly found in siloxane resins having the general formula $R_nSiO_{(4-n)/2}$. The hydroxy groups in these siloxane resins typically result from the reaction of the hydrolyzable group on the siloxane unit with water. The alkoxy groups result from partial hydrolysis when alkoxysilane precursors are used or from exchange of alcohol with hydrolysable groups. Typically, the weight percent of the total hydroxy groups present in the silsesquioxane resin wax is up to 10%. Typically, the weight percent of the total alkoxy groups present in silsesquioxane resin wax is up to 20%.

The molecular weights of the silsesquioxane resin wax are not restricted, but typically the number average molecular weight ($M_N$) range from 750 to 10,000, or alternatively from 1,000 to 5,000.

The silsesquioxane resin wax of the present invention can be prepared by any of the methods known in the art for preparing siloxane resins having the general formula $R_nSiO_{(4-n)/2}$ where R is an alkyl or aryl group and n is generally less than 1.8. Alternatively, the silsesquioxane resin wax can be prepared by the methods of the present invention as described infra.

The silsesquioxane resin wax of this invention are illustrated by a silsesquioxane resin wax comprising the units;

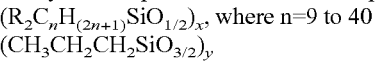

a silsesquioxane resin wax comprising the units;

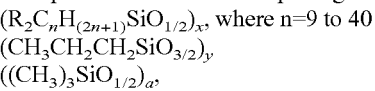

a silsesquioxane resin wax comprising the units;

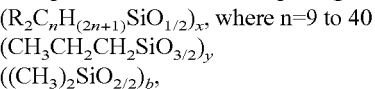

a silsesquioxane resin wax comprising the units;

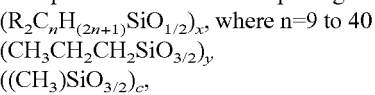

a silsesquioxane resin wax comprising the units;
$(R_2C_nH_{(2n+1)}SiO_{1/2})_x$, where n=9 to 40
$(CH_3CH_2CH_2SiO_{3/2})_y$
$(SiO_{4/2})_d$ a silsesquioxane resin wax comprising the units;
$(R_2C_nH_{(2n+1)}SiO_{1/2})_x$, where n=9 to 40
$(CH_3CH_2CH_2SiO_{3/2})_y$
$((CH_3)_3SiO_{1/2})_a$,
$(SiO_{4/2})_d$ a silsesquioxane resin wax comprising the units;
$(R_2C_nH_{(2n+1)}SiO_{1/2})_x$, where n=9 to 40
$(CH_3CH_2CH_2SiO_{3/2})_y$
$((CH_3)_3SiO_{1/2})_a$,
$((CH_3)SiO_{3/2})_c$, a silsesquioxane resin wax comprising the units;
$(R_2C_nH_{(2n+1)}SiO_{1/2})_x$, where n=9 to 40
$(CH_3CH_2CH_2SiO_{3/2})_y$
$((CH_3)_3SiO_{1/2})_a$,
$((CH_3)_2SiO_{2/2})_b$, a silsesquioxane resin wax comprising the units;
$(R_2C_nH_{(2n+1)}SiO_{1/2})_x$, where n=9 to 40
$(CH_3CH_2CH_2SiO_{3/2})_y$
$((CH_3)_2SiO_{2/2})_b$,
$((CH_3)SiO_{3/2})_c$, a silsesquioxane resin wax comprising the units;
$(R_2C_nH_{(2n+1)}SiO_{1/2})_x$, where n=9 to 40
$(CH_3CH_2CH_2SiO_{3/2})_y$
$((CH_3)_2SiO_{2/2})_b$,
$(SiO_{4/2})_d$ a silsesquioxane resin wax comprising the units;
$(R_2C_nH_{(2n+1)}SiO_{1/2})_x$, where n=9 to 40
$(CH_3CH_2CH_2SiO_{3/2})_y$
$((CH_3)SiO_{3/2})_c$,
$(SiO_{4/2})_d$ a silsesquioxane resin wax comprising the units;
$(R_2C_nH_{(2n+1)}SiO_{1/2})_x$, where n=9 to 40
$(CH_3CH_2CH_2SiO_{3/2})_y$
$((CH_3)_3SiO_{1/2})_a$,
$((CH_3)_2SiO_{2/2})_b$,
$((CH_3)SiO_{3/2})_c$, and
$(SiO_{4/2})_d$ a silsesquioxane resin wax comprising the units;
$(R_2C_nH_{(2n+1)}SiO_{1/2})_x$, where n=9 to 40
$(CH_3CH_2CH_2SiO_{3/2})_y$
$(C_6H_5SiO_{3/2})_c$ a silsesquioxane resin wax comprising the units;
$(R_2C_nH_{(2n+1)}SiO_{1/2})_x$, where n=9 to 40
$(CH_3CH_2CH_2SiO_{3/2})_y$
$((CH_3)(C_6H_5)SiO_{2/2})_b$, wherein a, b, c, and d have value of zero to 0.4, x and y have a value of 0.05 to 0.95,
with the provisos that the value of x+y is equal to or greater than 0.40, and the value of a+b+c+d+x+y=1, and R is equal to an alkyl group having from 1 to 8 carbon atoms, an aryl group, a carbinol group, or an amino group.

In all the formulas illustrated above, the R' group is designated as being on the M siloxy unit. In another embodiment of the present invention, the R' group can be on either a D or T siloxy unit.

The present invention also provides a method for preparing a silsesquioxane resin wax. The method comprises reacting;

A) a SiH containing alkyl silsesquioxane resin,
B) a $C_9$-$C_{40}$ vinyl terminated hydrocarbon,
C) a hydrosilylation catalyst, and optionally
D) a solvent.

The reaction is illustrated by the following general scheme;

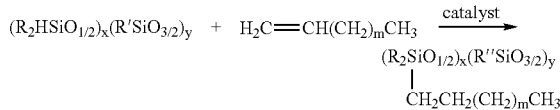

where m=6-37, and a, x, y, R, and R" are as defined above.

Component A), the SiH containing alkyl silsesquioxane resin, can be prepared by any of the methods known in the art to prepare such resins, but typically are prepared by one of two techniques. In the first technique, an alkylsilane having three hydrolyzable groups such as a halogen or alkoxy group present in the alkylsilane molecule is co-hydrolyzed with a hydrogen containing silane or siloxane. For example, the SiH containing alkyl silsesquioxane resins can be obtained by the acid catalyzed reaction of an alkyltrialkoxysilane, such as propyltrimethoxysilane, with tetramethyldisiloxane. In the second technique, an SiH containing silane or siloxane is equilibrated with a pre-formed alkyl silsesquioxane resin. For example, tetramethyldisiloxane can be reacted with a propyl silsesquioxane resin to yield a SiH containing propyl silsesquioxane resin.

The additional M, D, T, and Q units, as described supra, can be introduced into the silsesquioxane resin wax by incorporating such units into the SiH containing alkyl silsesquioxane resin precursor by reacting an additional organosilane(s), selected to produce the desired siloxy unit in the resulting resin during the co-hydrolysis of the propylsilane and SiH silane or siloxane. For example, reacting methoxytrimethylsilane, dimethoxydimethylsilane, trimethoxymethylsilane, tetramethoxysilane (or alternatively the corresponding ethoxy or chlorosilane of each) will respectively introduce a M, D, T, or Q unit into the SiH containing alkyl silsesquioxane resin. The amount of these additional silanes present in the co-hydrolysis reaction is selected to meet the mole fraction definitions, as described supra.

Alternatively, the SiH containing alkyl silsesquioxane resin can be prepared by reacting a preformed alkyl silsesquioxane, an SiH containing silane or siloxane, and other siloxanes containing various M, D, T, and Q units using any method in the art known to effect reaction of M, D, T, and Q siloxane units.

The SiH containing alkyl silsesquioxane resin is reacted with component B), a vinyl terminated hydrocarbon in the presence of a hydrosilylation catalyst. Typically, the vinyl terminated hydrocarbon has the formula $H_2C=CH(CH_2)_mCH_3$, where m is 6-37. The vinyl terminated hydrocarbons known as alpha olefins having 6 to 40 carbon atoms or blends there of can be used. The vinyl terminated hydrocarbons are illustrated by Amoco Chemical Company's Alpha-Olefin Products, Chevron Phillips Chemical Company Alpha olefin $C_{20-24}$, $C_{24-28}$, $C_{26-28}$, $C_{30+}$, $C_{30+HA}$, and Mitsui Chemicals America, Inc Tafmer®, to name a few.

The amounts of vinyl terminated hydrocarbon and SiH containing alkyl silsesquioxane resin can vary, but typically a molar excess of the vinyl terminated hydrocarbon is used vs. the amount of the SiH containing alkyl silsesquioxane resin in the hydrosilylation reaction to ensure complete reaction of all SiH in the reaction. Alternatively the vinyl terminated hydrocarbon is used in a 30%, or alternatively 10% molar excess vs. the amount of the SiH containing alkyl silsesquioxane resin The hydrosilylation catalyst is illustrated by any metal-containing catalyst which facilitates the reaction of silicon-bonded hydrogen atoms of the SiH containing alkyl silsesquioxane resin with the terminal vinyl groups of the vinyl terminated hydrocarbon. The metals are illustrated by ruthenium, rhodium, palladium, osmium, iridium, or platinum.

The metal-containing catalyst is typically a platinum-containing catalyst since they are the most widely used and available and because they provide a more favorable effect for the compositions of this invention in terms of improved reaction rates. Platinum-containing catalysts can be a compound or complex of a platinum metal.

One type of typical platinum-containing catalyst in the compositions of this invention is the composition that is obtained when chloroplatinic acid is reacted with an aliphatically unsaturated organosilicon compound such as divinyltetramethyldisiloxane, because of its easy dispersibility in organosilicon systems.

Preferably the hydrosilylation catalyst is selected from chloroplatinic acid, alcohol modified chloroplatinic acids, olefin complexes of chloroplatinic acid, complexes of chloroplatinic acid and divinyltetramethyldisiloxane, fine platinum particles adsorbed on carbon carriers, platinum supported on metal oxide carriers such as $Pt(Al_2O_3)$, platinum black, platinum acetylacetonate, platinum(divinyltetramethyldisiloxane), platinous halides exemplified by $PtCl_2$, $PtCl_4$, $Pt(CN)_2$, complexes of platinous halides with unsaturated compounds exemplified by ethylene, propylene, and organovinylsiloxanes, styrene hexamethyldiplatinum, and $RhCl_3$ $(Bu_2S)_3$.

The amount of hydrosilylation catalyst that is used is not narrowly limited as long as there is a sufficient amount to accelerate a reaction between the vinyl terminated hydrocarbon and the SiH containing alkyl silsesquioxane resin at room temperature or at temperatures above room temperature. The exact necessary amount of this catalyst will depend on the particular catalyst utilized and is not easily predictable. However, for platinum-containing catalysts the amount can be as low as one weight part of platinum for every one million weight parts of components the vinyl terminated hydrocarbon and the SiH containing alkyl silsesquioxane resin. The catalyst can be added at an amount 1 to 120 weight parts per one million parts of components the vinyl terminated hydrocarbon and the SiH containing alkyl silsesquioxane resin, but is typically added in an amount from 2 to 60 weight parts per one million parts of the vinyl terminated hydrocarbon and the SiH containing alkyl silsesquioxane resin.

The hydrosilyation reaction can be conducted neat or in the presence of D), a solvent. The solvent can be an alcohol such as methanol, ethanol, isopropanol, butanol, or n-propanol, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride, chloroform, dimethyl sulfoxide, dimethyl formamide, acetonitrile, tetrahydrofuran, white spirits, mineral spirits, or naphtha.

The amount of solvent can be up to 50 weight percent, but is typically from 20 to 50 weight percent, said weight percent being based on the total weight of components in the hydrosilylation reaction. The solvent used during the hydrosilylation reaction can be subsequently removed from the resulting silsesquioxane resin wax by various known methods.

The silsesquioxane resin wax are useful in a variety of personal, household, automotiveor medical care compositions. The silsesquioxane resin wax can be used either neat, or dispersed in a carrier. Typically, the carrier is selected from a volatile siloxane or organic solvent. The volatile siloxane solvent can be a cyclic polysiloxane, a linear polysiloxane, low molecular weight silsesquioxanes or Q siloxane structures, such as $TM_3$ or $M_4Q$, or mixtures of any of the above thereof. Some representative volatile linear polysiloxanes are hexamethyldisiloxane, octamethyltrisiloxane, decamethyltetrasiloxane, tetradecamethylhexasiloxane, and hexadecamethylheptasiloxane. Some representative volatile cyclic polysiloxanes are hexamethylcyclotrisiloxane, octamethylcyclotetrasiloxane, decamethylcyclopentasiloxane, and dodecamethylcyclohexasiloxane. The organic solvent can be an alcohol such as methanol, ethanol, isopropanol, butanol, or n-propanol, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, an acetate, such as ethyl acetate or butyl acetate, a halogenated hydrocarbon such as dichloromethane, 1,1,1-trichloroethane or methylene chloride, chloroform, dimethyl sulfoxide, dimethyl formamide, acetonitrile, tetrahydrofuran, or an aliphatic hydrocarbon such as white spirits, mineral spirits, isododecane, heptane, hexane or naphtha. Typically, the carrier is decamethylcyclopentasiloxane or isododecane. The silsesquioxane resin wax can be a paste, soft solid or solid dispersion in a carrier also.

The alkyl silsesquioxane resin wax can be used in antiperspirants, deodorants, skin creams, skin care lotions, moisturizers, facial treatments such as acne or wrinkle removers, personal and facial cleansers, sunscreens, make-ups, color cosmetics, foundations, blushes, lipsticks, lip balms, eyeliners, mascaras, and powders. Furthermore, it is anticipated that the compositions of the present invention can be combined with various other components to prepare the personal care or medical care products described infra. These components include, silicones materials, fragrances, preservatives, polyols, such as glycerin and propylene glycols, additional surfactants, moisturizers, pigments and powders, sunscreens, fragrances, emollients, structurants, thickeners, elastrolytes, pH control agents, film formers, conditioning agents, botanicals (plant extracts)) and actives such as vitamins and their derivatives, antioxidants and the like, amino-acids derivatives, liposomes, antiperspirant and deodorant agents, skin bleaching agent, skin protectants, self tanning agents, and conditioning agents for hair and skin such as quaternary polymer or amino functional silicones, commonly used to formulate such personal care and medical products. This silsesquioxane resin wax is used in amounts of from 0.1 to 20 parts by weight, preferably from 0.5 to 10 parts by weight, most preferably from 1 to 5 parts by weight.

The composition according to the invention may also be combined with a number of optional ingredients:

non-volatile polysiloxane having the structure:

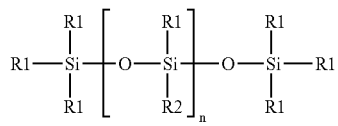

wherein n has a value sufficient to provide polysiloxane polymers having a viscosity in the range of 100-10,000 mm$^2$/sec. R1 and R2 can be alkyl radicals containing 1-20 carbon atoms or aryl groups, preferably alkyl radicals containing 1-6 carbon atoms, and more preferably methyl or phenyl groups. Typically, the value of n is 20-500, more preferably 80-375. Some illustrative polysiloxane polymers include polydimethylsiloxane, polydiethylsiloxane, polymethylethylsiloxane, polymethylphenylsiloxane, and polydiphenylsiloxane.

Alkylmethylsiloxanes: These siloxane polymers generally will have the formula Me$_3$SiO[Me$_2$SiO]$_y$[MeRSiO]$_z$SiMe$_3$, in which R is a hydrocarbon group containing 6-30 carbon atoms, Me represents methyl, and the degree of polymerization (DP), i.e., the sum of y and z is 3-50. Both the volatile and liquid species of alkymethysiloxanes can be used in the composition.

Silicone gums: Polydiorganosiloxane gums are known in the art and are available commercially. They consist of generally insoluble polydiorganosiloxanes having a viscosity in excess of 1,000,000 centistoke (mm$^2$/s) at 25° C., preferably greater than 5,000,000 centistoke (mm$^2$/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistokes (mm$^2$/s) at 25° C., to about 20 million centistokes (mm$^2$/s) at 25° C. Compositions of this type in the form of suspensions are most preferred, and are described for example in U.S. Pat. No. 6,013,682 (Jan. 11, 2000).

Silicone polyamides: Representative compositions of suitable silicone polyamide copolymers are set forth in detail in U.S. Pat. No. 5,981,680 (Nov. 9, 1999).

Silicone resins: These resin compositions are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for applications herein are generally supplied in an unhardened form in low viscosity volatile or nonvolatile silicone fluids. The silicone resins should be incorporated into compositions of the invention in their non-hardened forms rather than as hardened resinous structures.

Silicone elastomers: Such elastomers are generally reaction products obtained by combining an organopolysiloxane having an unsaturated group bound to a terminal silicon atom and an organohydrogensiloxane, and then subjecting it to at least a partial cure. One example of a suitable elastomer is a composition known in the cosmetic industry under its INCI name of Dimethicone/Vinyl Dimethicone Crosspolymer or Dimethicone Crosspolymer. Emulsions and suspension of these polysiloxane elastomers can also be used as components of the composition. Polysiloxane elastomers in the form of powders coated with different organic and inorganic materials such as mica and silica can also be used.

Carbinol Fluids: These materials are described in WO 03/101412 A2, and can be commonly described as substituted hydrocarbyl functional siloxane fluids or resins.

Water soluble or water dispersible silicone polyether compositions: These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible Compositions according to the invention can be provided in the form of water-in-oil or water-in-silicone emulsions using silicone emulsifiers. Typically, the water-in-silicone emulsifier is non-ionic and selected from the group comprising polyoxyalkylene-substituted silicones, silicone alkanolamides, silicone esters and silicone glycosides. Suitable silicone-based surfactants are well known in the art, and have been described for example in U.S. Pat. No. 4,122,029 (Gee et al.), U.S. Pat. No. 5,387,417 (Rentsch), and U.S. Pat. No. 5,811,487 (Schulz et al.) and include polydiorganosiloxane polyoxalkylene copolymers containing at least one polydiorganosiloxane segment consisting essentially of R$_b$SiO$_{(4-b)2}$ siloxane units wherein b has a value of from 0 to 3, inclusive, there being an average value of approximately 2 R groups per silicon for all siloxane units in the copolymer, and R denotes a radical selected from the group consisting of methyl, ethyl, vinyl, phenyl, and a divalent radical bonding a polyoxyalkylene segment to the polydiorganosiloxane segment, at least 95 percent of all R being methyl; and at least one polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8. Alternatively the silicone-based surfactant can be a cross-linked emulsifier in which at least two organopolysiloxane-polyoxyalkylene molecules are cross-linked by a cross-linking radical; the crosslinked organopolysiloxane-polyoxyalkylene emulsifier having the formula

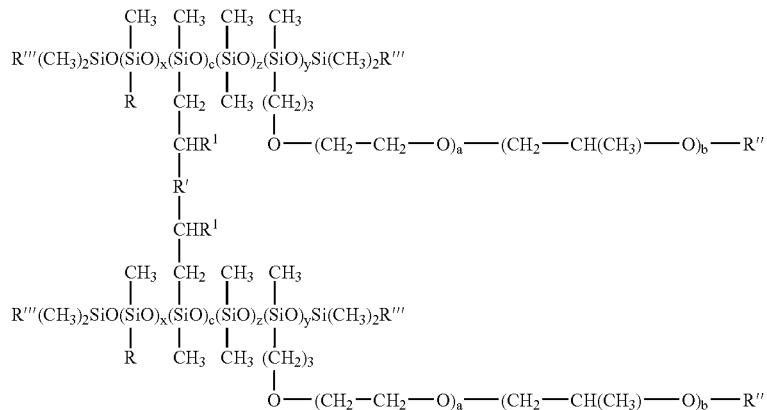

wherein the crosslinked organopolysiloxane-polyoxyalkylene emulsifier formula R is an aliphatic radical having 2 to 25 carbon atoms; R' is an organic or organosiloxane group which does not contain hydrolyzable bonds; R" is a terminal group; R'" is independently an aliphatic radical having 1 to 25 carbon atoms; $R^1$ is independently selected from the group consisting of hydrogen and an aliphatic radical containing 1-3 carbon atoms; x is an integer from 0 to 100; c is an integer from 1 to 5; z is an integer from 0 to 600; y is an integer from 1 to 10; x+y+z>40; a is an integer from 4 to 40; b is an integer from 0 to 40; a/b>1. The amount of the silicone emulsifying agent in the final composition may vary widely, but typically would be from 0.05% to 1.5%, preferably 0.1 to 1%, more preferably 0.15 to 0.8% by weight, most preferably 0.2 to 0.6% by weight.

The composition according to the invention can include a sunscreen as an optional or as a main ingredient. Sunscreens include but are not limited to those components which absorb ultraviolet light between 290 and 320 nanometers, i.e., the UV-B region, such as para-aminobenzoic acid derivatives and cinnamates derivatives such as ethyl hexyl methoxy cinnamate; and those compositions which absorb ultraviolet light in the range of 320 to 400 nanometer, i.e., the UV-A region, such as benzophenone derivatives and butyl methoxy dibenzoylmethane derivatives, and hydrophilic compositions such as benzylidine-2-camphor sulphonic acid derivatives. The cosmetic compositions according to the invention can also contain pigments or alternatively nanopigments (average primary particle size: generally between 5 nm and 100 nm, preferably between 10 and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminum When the composition according to the invention is an oil-in-water emulsion, it will include common ingredients generally used for preparing emulsions such as but not limited to nonionic surfactants well known in the art to prepare oil-in-water emulsions. Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

Compositions according to the invention can include suspending agents such xanthan gum, carboxyvinyl polymers. Examples of these polymers include Carbopol 934, 940, 941, and 956. available from B. F. Goodrich Company. Still other suitable suspending agents include di(hydrogenated tallow) phthalic acid amide, and crosslinked maleic anhydride-methyl vinyl ether copolymer, cellulose ethers derivatives, guar gum, polyvinyl alcohol, polyvinyl pyrrolidone, hydroxypropyl guar gum, starch and starch derivatives, Suitable thickening agents are exemplified by sodium alginate, gum arabic, polyoxyethylene, guar gum, hydroxypropyl guar gum, ethoxylated alcohols, such as laureth-4 or polyethylene glycol 400.

The composition according to the invention can further contain an oil or oily component. The term oil as used herein refers to any material that is substantially insoluble in water, and which is generally compatible with any low molecular weight silicone species present in the composition. When the composition is to be used in a cosmetic or personal care product, the product components must also be cosmetically acceptable, or otherwise meet the conditions of the end use of the product. Some example of suitable oil components include natural oils such as coconut oil; hydrocarbons such as mineral oil and hydrogenated polyisobutene; fatty alcohols such as octyldodecanol; esters such as C12 to C15 alkyl benzoates; diesters such as propylene dipelargonate; and triesters such as glyceryl trioctanoate. Low viscosity oils can also be used such as those oils having a viscosity of 5 to 100 mPa·s at 25° C., generally consisting of esters having a structure such as RCO—OR' wherein RCO represents a carboxylic acid radical and OR' is an alcohol residue.

Some examples of low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol and mixtures of octyldodecanol, Caprylic/Capric triglycerides, isododecanol, soybean oil, sunflower oil, wheat and/or cereal germ oil, sweet almond oil, jojoba oil, avocado oil, olive oil, palm oil, calophyllum, and castor oil.

Other additives can include powders and pigments especially when the composition according to the invention is intended to be used for make-up. The powder component of the invention can be generally defined as dry, particulate matter having a particle size of 0.02-50 microns. The particulate matter may be colored or non-colored (for example white). Suitable powders include but not limited to bismuth oxychloride, titanated mica, fumed silica, spherical silica beads, polymethylmethacrylate beads, boron nitride, aluminum silicate, aluminum starch octenylsuccinate, bentonite, kaolin, magnesium aluminum silicate, silica, talc, mica, titanium dioxide, kaolin, nylon, silk powder. The above mentioned powders may be surface treated to render the particles hydrophobic in nature.

The powder component also comprises various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent coloring agent, such as carbon black, chromium or iron oxides, ultramarines, manganese pyrophosphate, iron blue, and titanium dioxide, pearlescent agents, generally used as a mixture with colored pigments, or some organic dyes, generally used as a mixture with colored pigments and commonly used in the cosmetics industry, can be added to the composition. In general, these coloring agents can be present in an amount by weight from 0 to 20% with respect to the weight of the final composition.

Pulverulent inorganic or organic fillers can also be added, generally in an amount by weight from 0 to 40% with respect to the weight of the final composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked, copolymer microspheres such as EXPANCEL (Nobel Industrie), polytrap and silicone resin powder and microbeads (TOSPEARL from Toshiba, for example).

The waxes or wax-like materials useful in the composition according of the invention have generally have a melting point range of 35 to 120° C. at atmospheric pressure. Waxes in this category include synthetic wax, ceresin, paraffin, ozokerite, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. Mention may be made, among the waxes capable of being used as non-silicone fatty substances, of animal waxes, such as beeswax; vegetable waxes, such as carnauba, candelilla wax; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

Silicone silsesquioxane resin wax can also be used in antiperspirant and deodorant compositions under but not limited to the form of sticks, soft solid, roll on, aerosol, pumpspray. Some examples of antiperspirant agents and deodorant agents are Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, Zinc Ricinoleate.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics, are also well known standard methods, including washing, wiping, peeling and the like.

For use on the skin, the compositions according to the present invention may be used in a conventional manner for example for conditioning the skin. An effective amount of the composition for the purpose is applied to the skin. Such effective amounts generally range from about 1 mg/cm$^2$ to about 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from about 1 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit. When a high silicone content is incorporated in a hair care composition according to the invention, this may be a useful material for split end hair products.

The compositions according to this invention can be used on the skin of humans or animals for example to moisturize, colour or generally improve the appearance or to apply actives, such as sunscreens, deodorants, insect repellents, etc.

The silsesquioxane resin waxes are particularly useful to enhance the durability and substantivity of cosmetics in topical formulations and can be used as structurants in cosmetics. They can also be used in household care items such as polishes, waxes, vinyl and leather treatments and in wax control in crude oil recovery. They can also be used in automotive care items such as polishes, waxes, vinyl, leather, and tire treatments and protectants.

EXAMPLES

The following examples are presented to further illustrate the compositions and methods of this invention, but are not to be construed as limiting the invention. All parts and percentages in the examples are on a weight basis and all measurements were obtained at about 23° C., unless indicated to the contrary.

The representative silsesquioxane resin waxes (intermediates to prepare them) of these examples are described using the M, D, T, and Q designation for the siloxy units present in the resin. The superscripts further describe the alkyl substitute present on the siloxy unit. The superscripts used herein designate the following; Pr is $CH_3CH_2CH_2$—, H is hydrogen (as $\equiv$SiH). The subscripts describe the mole fraction of the siloxy unit in the resin.

Materials $T^{Pr}$ RESIN=propyl silsesquioxane resin at 71.0 wt % in toluene. The propyl silsesquioxane resin (abbreviated herein as $T^{Pr}$) has the formula $CH_3CH_2CH_2SiO_{3/2}$ with a $M_N$ of 3500 and 7 wt % of OH groups was prepared from the hydrolysis of propyl trichlorosilane.

C18 olefin represents; $H_2C$=$CH(CH_2)_{15}CH_3$ 1-octyldecene, was used as received from Chevron Phillips Chemical Company, 10001 Six Pines Drive, The Woodlands, Tex. 77380.

C20-C24 olefin represents; $H_2C$=$CH(CH_2)_{20-24}CH_3$ was used as received from Chevron Phillips Chemical Company, 10001 Six Pines Drive, The Woodlands, Tex. 77380.

C26-C28 olefin represents; $H_2C$=$CH(CH_2)_{26-28}CH_3$ was used as received from Chevron Phillips Chemical Company, 10001 Six Pines Drive, The Woodlands, Tex. 77380.

C30+ olefin represents; CAS # 260255-62-7, was used as received from Chevron Phillips Chemical Company, 10001 Six Pines Drive, The Woodlands, Tex. 77380.

Example 1 (Reference)

Preparation of $MM^HT^{Pr}$ Resins from $T^{Pr}$ Silsesquioxane Resin

A 3-neck reaction flask equipped with an agitator, temperature probe, Dean Stark trap and condenser was charged with a T propyl resin, hexamethyldisiloxane, tetramethyl-dihydrogendisiloxane and water at the ratios shown in Table 1. The Dean Stark trap was pre-loaded with toluene to insure the solids level was maintained. Trifluoromethanesulfonic acid was added as the catalyst at 0.01 wt % to the reaction mixture in the flask. The temperature of the reaction mixture was maintained at or below 50° C. with a water bath initially as needed. When the temperature stabilized, the temperature was maintained at 50° C. for 3 hours. Then, the reaction mixture was heated at reflux (100-140° C.) and water removed via the Dean Stark trap as needed. After all the water formed in the reaction was removed, the resin mixture was allowed to cool and a 10×molar excess of calcium carbonate (9.31 g to 700 microliters of FC-24) to neutralize the acid catalyst. The resin mixture was then filtered through a pressure filter and volatiles removed via a rotary evaporator.

TABLE 1

| Example # | Wt % of $T^{Pr}$ Resin | Wt % of Hexamethyl-disiloxane | Wt % of Tetramethyl-dihydrogen-disiloxane | Ratio of $Me_3Si$ to $Me_2HSi$ disiloxane | Wt % of Water |
|---|---|---|---|---|---|
| 1-1 | 77.4 | 16.5 | 1.5 | 90:10 | 4.6 |
| 1-2 | 78.3 | 9.3 | 7.7 | 50:50 | 4.7 |
| 1-3 | 79.6 | 0 | 15.6 | 0:100 | 4.8 |
| 1-4 | 77.6 | 14.7 | 3.1 | 80:20 | 4.6 |

Example 2 (Reference)

Preparation of $MM^HT^{Pr}$ Resin from Propyl Trimethoxysilane

A 3-neck reaction flask equipped with an agitator, temperature probe, addition funnel and a condenser was charged with propyl trimethoxysilane, hexamethyldisiloxane, tetramethyldihydrogendisiloxane and FC-24 catalyst at the ratios in Table 1. Water was then added via the addition funnel. The temperature was maintained below 50° C. by regulation of water addition and use of water bath if needed. After the water addition, the temperature was maintained 50° C. for 3 hours. The resulting two phase reaction mixture was then placed in a separatory funnel to separate the aqueous phase from the resin phase. Heptane was added in sufficient amounts to help separate excess water from resin. The collected resin phase was then put back in 3-neck flask and a 10×molar excess $CaCO_3$ was added to neutralize any remaining acid catalyst. Water was also added to remove any methoxy present, and the mixture heated to reflux (100-140° C.) with a Dean Stark trap in place to remove trace quantities of water and heptane. After cooling, $MgSO_4$ was added to remove any water that is present. Finally, the resin was passed through a pressure filter.

TABLE 2

| Example # Ratio of Me3 to Me2H | Wt % of Propyl-trimeth-oxysilane | Wt % of Hexamethyl-disiloxane | Wt % of Tetramethyl-dihydrogen-disiloxane | Wt % of FC-24 | Wt % of Water |
|---|---|---|---|---|---|
| 2-1 (0:100) | 47.3 | 0 | 21.6 | 0.01 | 31.1 |
| 2-2 (50:50) | 46.2 | 12.7 | 10.6 | 0.01 | 30.5 |

Example 3

$T^{Pr}$ Resin Waxes from $MM^HT^{Pr}$ Resins

This example describes the procedure used to prepare representative silsesquioxane resin waxes of the present invention. The formulations used and description of the olefinic wax is shown below in Table 3.

A 3-neck reaction flask equipped with an agitator, temperature probe, and a condenser was charged with a siloxane resin (as prepared via reference example 1 or 2) and sufficient heptane to reduce viscosity. The contents were then heated to 60-70° C. The olefinic wax was then added to the reaction flask and followed by addition of the platinum catalyst. After an initial exotherm, the temperature was maintained at 120° C. for 3-4 hours before checking the Si—H of the wax. The melt points of the resulting waxes were characterized by DSC, and shown in Table 4 below.

Comparative Example C-1

A 3-neck reaction flask equipped with an agitator, temperature probe, and a condenser was charged with olefinic wax. The contents were then heated to 75-85° C. and the platinum catalyst was added. A methylhydrogen linear siloxane fluid was then added through an addition funnel to the reaction. After an initial exotherm, the temperature was maintained at 120° C. for 3-4 hours and check Si—H of wax. The formulation used is shown in Table 3.

TABLE 3

| Example # (Resin Used, Wax used) | Wt % of $T^{Pr}$ Si—H Resin | Wt % of Si—H Fluid | Wt % of Wax | Wt % of Platinum Catalyst |
|---|---|---|---|---|
| C-1 | | 6.5 | 94.3 | 0.02 |
| 1-1, C30+ | 91.72 | | 8.28 | 0.02 |
| 1-1, C18 | 95.79 | | 4.21 | 0.02 |
| 1-2, C30+ | 65.84 | | 34.16 | 0.02 |
| 1-2, C18 | 79.85 | | 20.15 | 0.02 |
| 1-3, C30+ | 46.84 | | 53.16 | 0.02 |
| 1-3, C18 | 64.42 | | 35.58 | 0.02 |

TABLE 3-continued

| Example # (Resin Used, Wax used) | Wt % of T$^{Pr}$ Si—H Resin | Wt % of Si—H Fluid | Wt % of Wax | Wt % of Platinum Catalyst |
|---|---|---|---|---|
| 2-1, C20-24 | 31.67 | | 68.53 | 0.02 |
| 2-1, C26-28 | 24.73 | | 75.27 | 0.02 |
| 2-1, C30+ | 21.33 | | 78.67 | 0.02 |

TABLE 4

| Example # | Melt Point, ° C. |
|---|---|
| C-1 | 70 |
| 1-1, C30+ | 6, 44 |
| 1-1, C18 | −63 |
| 1-2, C30+ | 34, 45 |
| 1-2, C18 | −46, −11 |
| 1-3, C30+ | NA |
| 1-3, C18 | 56 |
| 2-1, C20-24 | 34 |
| 2-1, C26-28 | 56 |
| 2-1, C30+ | 66 |

Example 4

Silsesquioxane resin waxes have improved compatibility with volatile silicone compared to C-1 while maintaining its compatibility with other cosmetic ingredients, as shown in Table 5.

TABLE 5

Compatibility with Cosmetic Ingredients

| Material | Wax/material | C-1 | 2-1, C20-24 | 2-1, C26-28 | 2-1, C30+ |
|---|---|---|---|---|---|
| Beeswax | 1/9 | C | | | C |
|  | 5/5 | C | | | C |
|  | 9/1 | C | | | C |
| Ozokerite | 1/9 | C | | | C |
|  | 5/5 | C | | | C |
|  | 9/1 | C | | | C |
| Candellilla Wax | 1/9 | C | | | C |
|  | 5/5 | C | | | C |
|  | 9/1 | C | | | C |
| Castor oil | 1/9 | C | C | C | C |
|  | 5/5 | ~C | ~C | ~C | ~C |
|  | 9/1 | C | C | C | C |
| cyclomethicone | 1/9 | NC | | | C |
|  | 5/5 | C | | | C |
|  | 9/1 | C | | | C |
| Isododecane | 1/9 | C | | | C |
|  | 5/5 | C | | | C |
|  | 9/1 | C | | | C |
| Vitamin A Palmitate | 1/9 | C | | | C |
|  | 5/5 | C | | | C |
|  | 9/1 | C | | | C |

C = compatible,
NC = not compatible

Example 5

The Silsesquioxane resin wax is more compatible with solvents and fragrance components like cyclomethicone, benzaldehyde, benzyl acetate, and phenoxy ethanol than the alkyl methyl silicone wax, C-1. Therefore, the silsesquioxane resin wax is more suitable for thickening silicone-based systems than C-1. Also its improved compatibility with certain fragrance components gives a potential impact on fragrance retention. Table 6 summarizes representative examples tested.

TABLE 6

Compatibility with Fragrances

| | 2-1, C30+ | | | | |
|---|---|---|---|---|---|
| | | 80° C. | | RT | |
| | C-1 | 2 Perf/ 8wax | 5 Perf/5 wax | 2 Perf/ 8wax | 5 Perf/5 wax |
| | 80° C. | RT | | | | |
| limonene | M | M | M | M | M |
| benzaldehyde | N M | M | M | M | M |
| benzyl acetate | N M | M | M | M | M |
| decyl aldehyde | M | M | M | M | M |
| Iso E super | M | M | M | M | M |
| Phenoxy ethanol | N M | M | NM | M | NM |

M = miscible,
NM = not miscible

The Silsesquioxane resin wax is more compatible with solvents and fragrance components like cyclomethicone, benzaldehyde, benzyl acetate, and phenoxy ethanol than the alkyl methyl silicone wax, C-1. Therefore, the silsesquioxane resin wax would be more suitable for thickening silicone-based systems than C-1. Also its improved compatibility with certain fragrance components gives a potential impact on fragrance retention.

Example 6

Rheology Modifier for Oil-in-Water and Water-in-Oil Emulsions

TABLE 6

Oil in water emulsions containing sunscreen

| Ingredients | | Control 0% resin wax | 2-1, 30+ |
|---|---|---|---|
| Phase A | | | |
| Parsol MCX | Ethylhexyl Methoxycinnamate | 4.0% | 4.0% |
| Cithrol GMS/SE (croda) | Glyceryl stearate | 3.0% | 3.0% |
| Myritol 312 | Caprylic/Capric Triglyceride | 4.0% | 4.0% |
| Sepicide HB | | 0.5% | 0.5% |
| Silsesquioxane Resin Wax(2-1, 30+), or C-1 | C30+ | — | 2.0% |
| Phase B | | | |
| Amphisol K | Potassium Cetyl Phosphate | 2.0% | 2.0% |
| Phase C | | | |
| Carbopol 980 (Sol 1%) | Carbomer | 10.0% | 10.0% |
| Propylene glycol | | 3.5% | 3.5% |
| KOH Sol 10% | | q.s. pH 7 | q.s. pH 7 |
| Distilled water | | 31 | 37 |
| Phase D | | | |
| Dow Corning 245 | Cyclopentasiloxane | 6% | 4.0% |

TABLE 6-continued

Oil in water emulsions containing sunscreen

| Ingredients | Control 0% resin wax | 2-1, 30+ |
|---|---|---|
| Phase E | | |
| Water | 30% | 30% |
| Viscosity | 4700 cPs | 11,600 cPs |

Procedure:
1. Mix ingredients of phase A together and heat to 75° C.
2. Mix ingredients of phase C together and heat to 75° C.
3. Add phase B into phase A making sure that the temperature remains at 75° C.
4. Add phase C in to phase A + B under high agitation. When addition is complete, stop the heating.
5. Add the phase D to the above when the temperature is below 50° C. under high agitation
6. Add the phase E to the above under high agitation.
Adjust to pH 7 if necessary and compensate the loss of water due to heating.

TABLE 7

Water-in-Oil Emulsion

| Material | Wt % |
|---|---|
| Oil Phase | |
| Dow Corning245 | 10.0 |
| Dow Corning5225C | 10.0 |
| Silsesquioxane resin wax | 2.0 |
| Fragrance | 0.5 |
| Water Phase | |
| Glycerin | 5.0 |
| NaCl | 1.0 |
| DI Water | 72.5 |

Procedure:

Melt wax in DC 245, add hot mixture to DC 5225C while mixing with dual blade. Mix until dispersed. Increase mixing speed to 1376 RPM while adding water phase(water, NaCl and glycerin). Add water phase over 10 minutes. Mix for an additional 10 minutes.

Viscosity cream containing resin wax: 80,000 cPs
Viscosity cream control (no resin wax: 50,500 cPs These examples indicates that the resin silesquioxane wax act as a rheology modifier by increasing the viscosity of both oin-in-water and water-in-oil systems.

Example 7

Texture Modifier for Oil-in-Water and Water-in-Oil Creams.

Using a texture analyzer, oil-in-water and water-in-oil emulsions described in Table 6 and 7 have been compared to their control for the following parameters: Hardness, compressability, adheseiveness and cohesiveness.

Equipment: Texture analyzer
Stable Micro system
Software: Texture Expert Exceed
Probe used: 0.5 hemispherical stainless Procedure: The probe is mechanically dipped into the skin cream under analysis, penetrating to a depth of 10 mm into the cream at a constant speed (two dips at a slow speed and two dips at a fast speed) and the probe is returned to the start position. By repeating twice the penetration of the probe in the cream, the force is measured in the compression mode. This experiment is repeated on two others samples (40gr) of the same cream. Three results are obtained for each cream.

Using a macro data analysis, the following information was obtained:

Peak compressive force from the first indent gives information on the hardness of the cream Area under the first indent curve gives information on the compressibility of the cream Area under the withdrawal curve gives information on the adhesiveness of the cream Area under the second indent curve divided by the area under the first indent curve gives information on the cohesiveness of the cream.

TABLE 8

Texture analyzer results:

| | | Slow speed | Hardness Force (g) | Compressibility 1:2 area | Adhesiveness 2:3 area | 2nd penetration of the probe 4:5 area | Cohesiveness Divde 1:2 area by 4:5: area |
|---|---|---|---|---|---|---|---|
| Water in Oil | CONTROL | Mean | 8.28 | 22.09 | −13.04 | 19.62 | 1.12 |
| | | Stdev | 0.85 | 2.85 | 1.86 | 1.35 | 0.07 |
| | RESIN WAX | Mean | 14.71 | 40.04 | −22.69 | 34.56 | 1.16 |
| | | Stdev | 0.43 | 2.44 | 0.15 | 0.94 | 0.04 |
| Oil in Water | CONTROL | Mean | 10.47 | 5.69 | −3.22 | 5.39 | 1.05 |
| | | Stdev | 1.28 | 1.34 | 0.42 | 1.11 | 0.05 |
| | RESIN WAX | Mean | 19.01 | 12.31 | −3.95 | 11.74 | 1.05 |
| | | Stdev | 0.85 | 1.41 | 0.37 | 1.65 | 0.03 |

Summary: Compared to the control cream, the addition of resin wax significantly increases the hardness and the compressibility of the emulsion for improved stability but without increasing the cohesiveness allowing good spreadability of the cream on the skin. The impact on the adhesiveness is minimal for minimum film residue and low tack.

Example 8

Sunscreen Oil-in-Water Emulsion

TABLE 9

| Sunscreen: Water-in-Oil Emulsion | | |
|---|---|---|
| Ingredients | INCI Name | C-1 or 2-1, C30+ |
| *Phase A* | | |
| Parsol MCX | Ethylhexyl Methoxycinnamate | 4% |
| Sepicide HB | | 0.5% |
| Witconol TN | | 7.0% |
| DC 5200 | Lauryl PEG/PPG-18/18 Methicone | 2.0% |
| C-1 or Silsesquioxane Resin wax (2-1, C30+) | Silicone Wax | 2.0% |
| *Phase B* | | |
| Dow Corning 245 | Cyclopentasiloxane | 8.5% |
| *Phase C* | | |
| Propylene glycol | | 3.5% |
| NaCl | | 1.0% |
| Distilled water | | 71.5 |

Procedure:
1. To mix ingredients of phase A and heat to 60° C. under slow stirring (200 RPM)
2. Add phase B to phase A just before emulsifying.
3. To mix ingredients of phase C in another beaker and heat to 60° C.
4. Add Phase C very slowly into Phase A + B under very strong agitation (1900 rpm).
5. When addition is completed, leave under agitation for an additional 5 minutes and pass through a homogenizer.

Example 9

Formulation of the Silsesquioxane Resin Wax in Physical Sunscreens

TABLE 10

| Physical Sunscreen Formulation | | |
|---|---|---|
| Ingredients | INCI Name | |
| *Phase A* | | |
| Tioveil OP | Titanium Dioxide (and )C12-C15 Alkyl Banzoate andpolyhydrostearic Acid (and) Aluminium Stearate (and) Alumina. | 12.5% |
| Sepicide HB | | 0.5% |
| DC 5200 | Lauryl PEG/PPG-18/18 Methicone | 3.0% |
| | Mineral oil | 5.0% |
| Witconol TN | C12-C15 alkyl Benzoate | 6.0% |
| Silsesquioxane Resin wax (2-1, C30+) | C30+ | 2.0% |

TABLE 10-continued

| Physical Sunscreen Formulation | | |
|---|---|---|
| Ingredients | INCI Name | |
| *Phase B* | | |
| Propylene glycol | | 3.5% |
| NaCl | | 1.0% |
| Distilled water | | 66.5% |

Procedure:
1. To mix ingredients of phase A and heat to 60° C. under slow stirring (200 RPM).
2. To mix ingredients of phase B in another beaker and heat to 60° C.
3. Add Phase B very slowly into Phase A under very strong agitation (1900 rpm).
4. When addition is completed, leave under agitation for an additional 5 minutes and pass through a homogenizer.

Example 10

Formulation of the Silsesquioxane Resin Wax and Vitamins

TABLE 11

| Vitamin Formulation | | |
|---|---|---|
| Ingredients | INCI Name | |
| *Phase A* | | |
| | Vit A palmitate | 0.6% |
| Sepicide HB | | 0.5% |
| DC 5200 | Lauryl PEG/PPG-18/18 Methicone | 3.0% |
| | Mineral oil | 17.0% |
| Dow Corning ® 200 FL 5 cSt | Dimethicone | 5.0% |
| Silsesquioxane Resin wax (2-1, C30+) | C30+ | 4.0% |
| *Phase B* | | |
| Glycerine | | 3.0% |
| NaCl | | 1.0% |
| Distilled water | | 65.9% |

Procedure:
1. To mix ingredients of phase A and homogenise except Vit A Palmitate and heat to 60° C. under slow stirring (200 RPM).
2. To mix ingredients of phase B in another beaker and heat to 60° C.
3. Add Phase B very slowly into Phase A under very strong agitation (1900 rpm).
4. When addition is completed, add the Vit A Palmitate and leave under agitation for an additional 5 minutes and pass through a homogeniser.

Example 11

Foundation Cream with Silsesquioxane Resin Wax

TABLE 12

| Formulation of Foundation Cream | | |
|---|---|---|
| Ingredients | INCI Name | |
| *Phase A* | | |
| Dow Corning ® 1501 | Cyclomethicone (and) Dimethiconol | 10.0% |
| Dow Corning ® 245 Fluid | Cyclopentasiloxane | 3.0% |
| TiO2 W877 | Titanium dioxide | 11.0% |
| Yellow W 1802 | Iron Oxide | 2.5% |
| Red W 3801 | Iron Oxide | 1.5% |

TABLE 12-continued

Formulation of Foundation Cream

| Ingredients | INCI Name | |
|---|---|---|
| Black W 9801 | Iron Oxide | 0.6% |
| *Phase B* | | |
| Silsesquioxane Resin wax (2-1, C30+) | C30+ | 2.0% |
| Sepicide HB | | 0.5% |
| Dow Corning ® 5225 c | Cyclomethicone (and) PEG/PPG-18/18 Dimethicone | 10.0% |
| *Phase C* | | |
| | Polysorbate 20 | 0.5% |
| NaCl | | 1.0% |
| Distilled water | | 57.4% |

Procedure:
1. To mix ingredients of phase A and homogenize using a high shear mixer.
2. Heat phase A to 60° C. and add silsesquioxane resin Wax, when melted, add remain of phase B
3. To mix ingredients of phase C in another beaker and heat to 60° C.
4. Add Phase C very slowly into Phase A + B under very strong agitation (1900 rpm).
5. When addition is completed, leave under agitation for an additional 5 minutes and pass through a homogenizer Example 12

Lipstick Formulations

TABLE 13

Formulation of Cyclopentasiloxane-based Lipstick

| Products | | % |
|---|---|---|
| PHASE A | | |
| White ozokerite wax | | 4 |
| Cerilla G | candellila wax | 11 |
| Eutanol G | Octyl dod ecanol | 25 |
| Dow Corning 245 | Cyclopentasiloxane | 5 |
| Silsesquioxane Resin Wax (2-1, 30+) or C-1 | C30+ | 5 |
| Petrolatum (vaselium) | | 4 |
| Fluilan | lanolin oil | 9 |
| Avocado oil | | 2 |
| Novol | Oleyl alcohol | 8 |
| pigment blend | | 27 |
| | | 100 |
| PHASE B | | |
| Covasil TiO2 | | 5 |
| Dow Corning 245 | | 77.5 |
| Covasil red W3801 | | 17.5 |
| | | 100 |

Procedure
1. Heat phase A to 85 C.
2. Add Phase B
3. Pour formulation into lipstick mold
4. Place in freezer for 60 min.
5. Remove from molds

TABLE 14

Formulation of Castor oil-based Lipstick

| | | % |
|---|---|---|
| Phase A | | |
| castor oil | | 43.7 |
| softisan 100 | Hydrogenated coco-glycerides | 8 |
| cerilla G | Candelilla Cera | 9 |
| softisan 645 | Bis-Diglyderyl Polyacyladipate | 8 |
| cerabeil blanchie DAB | Cera alba | 3 |
| Cerauba T1 | Cera Carnauba | 2 |
| Trivent OC-G | Ticaprylin | 15 |
| Vitamin E acetate | Tocopheryl acetate | 0.5 |
| Propyl paraben | | 0.1 |
| | BHT(2,6-di-tert-butyl-4-methylphenol) | 0.05 |
| Silsesquioxane Resin Wax (2-1, 30+) or C-1 | C30+ | 5 |
| | | 94.3 |
| Phase B | | |
| COD 8008 | White | 1 |
| COD 8005 | Yellow | 3 |
| COD 8006 | Red | 1.7 |
| COD 8004 | Black | 0 |
| | | 5.7 |

Procedure
1. Heat phase A to 85 C.
2. Add Phase B
3. Pour into lipstick molds
4. Place in freezer for 60 min.
5. Remove from molds.

Transfer Resistance Testing for Lipsticks

Procedure: 14 panelists are required for two comparisons of 2 formulations (one comparison on each forearm). The panelist must evaluate different criteria:
1. Ease of application: the panelist is asked to apply the lipsticks himself/herself by making one line of each on the back of his non-dominant hand and to indicate which is the easiest product to apply.
2. Non-transfer: the operator applies a microscope slide on the 2 spots of lipstick for 10 sec; the panelist then indicates which product he/she considers is the least transferred onto the slide.

If 13 panelists out of 14 chose A, a difference occurs at a significance level of 0.1%.

If 12 panelists out of 14 chose A, a difference occurs at a significance level of 1%.

If 11 panelists out of 14 chose A, a difference occurs at a significance level of 5%.

TABLE 15

Non-Transfer Results of Lipstick Formulations

| | Combinations | Ease of application | Non transfer |
|---|---|---|---|
| Cyclopentasiloxane-based lipstick | 2-1, C30+ | 10 | 7 |
| | C-1 | 4 | 7 |
| Castor oil-based lipstick | 2-1, C30+ | 4 | 14 |
| | C-1 | 10 | 0 |

Summary

The silsesquioxane resin wax was as easy as C-1 to incorporate into both lipstick formulations. The cyclopentasiloxane based lipstick with the silsesquioxane resin wax showed superior ease of application and the castor oil based lipstick showed superior non-transfer properties over C-1.

Example 13

Household or Automotive Care Products

Silsesquioxane resin wax samples were delivered in solvent at 10% solids and applied to aluminum panel and vinyl squares and tested for coefficient of friction (CoF), contact angle and gloss.

TABLE 16

Gloss & CoF of Thin Film on Aluminum

| Example#* | Appearance | Static CoF** | Kinetic CoF** | 20° Gloss | 60° Gloss | 85° Gloss |
|---|---|---|---|---|---|---|
| 2-1, C30+ | Even coating/white wax film/dry | 0.848 | 0.777 | 2.7 | 5.4 | 2.7 |
| 2-1, C26-28 | Even coating/white waxy film/dry | 0.52 | 0.452 | 4.2 | 9.4 | 6.2 |
| 2-1, C20-24 | Dry/white/waxy film | 0.784 | 0.681 | 7.0 | 16.2 | 50.7 |

*Applied from a 10% solution in solvent and allowed to dry

TABLE 17

Contact Angle of Various Liquid on Thin Film Applied to a Aluminum Panel

| Example#* | Dispersive (dyne/cm) | Polar (dyne/cm) | Surface Energy (dyne/cm) | H20 (degrees) | Meth Iodide (degrees) | Hexadecane (degrees) |
|---|---|---|---|---|---|---|
| 1-1, C30+ | 21.2 | 5.8 | 27 | 97.83 | 81.33 | 27.17 |
| 1-1, C18 | 23.7 | 2.2 | 25.9 | 100.33° | 64° | 35.17° |
| 2-1, C30+ | 22.6 | 0.1 | 22.7 | 116.5° | 73.5° | <15° |
| 2-1, C26-28 | 26.6 | 3.2 | 29.8 | 98.83° | 57.29° | 25.33° |
| 2-1, C20-24 | 27.1 | 3.5 | 30.6 | 96.33 | 56.17 | 22.33 |

*Applied from a 10% solution in solvent and allowed to dry

TABLE 18

Gloss of Thin Film on Vinyl

| Example #* | Appearance | 20° Gloss | 60° Gloss | 85° Gloss |
|---|---|---|---|---|
| 2-1, C30+ | Dry waxy feel/matte/even | 0.3 | 1.5 | 2.3 |
| 2-1, C26-28 | White/matte/no tack | 0.4 | 3.3 | 4.9 |
| 2-1, C20-24 | Matte/waxy feel | 0.5 | 4.5 | 6.1 |
| Dow Corning 200 Fluid, 350 cst | Shiny, greasy | 2 | 17.1 | 23.9 |

*Applied from a 10% solution in solvent and allowed to dry

Test method for Gloss, Contact Angle, and CoF:

The resulting films were characterized by visual observations and measurements of 20°, 60°, 80° Gloss with a Gardner Tri-Gloss Meter.

The VCA 2000 video contact-angle equipment by Advanced Surface Technology Inc., USA, was used (also known as a goniometer) to measure surface energy and contact angle The contact angle is measured at the interface of the film and three probe liquids: deionized water, reagent grade methylene diiodide, and reagent grade hexadecane. The probe liquids are delivered as a single droplet (~0.1-0.2 microliter) from a syringe mounted at a degree angle to the film surface. A digital image is captured immediately and contact angle measured. The average of three drops per fluid is reported. Surface energy is calculated from the three probe liquid contact angles using the Owens/Wendt method or the Geometric Method program on the SE 2000 software.

Coefficient of Friction (COF) measurements were obtained using a Monitor Slip and Friction Tester, Model 32-06 from Testing Machines, Inc. A 3 inch by 6 inch aluminum panel was placed under the clamp. Four layers of cheesecloth were attached under the "B" sled, which weighs 200 grams. Measurements were taken at 6 inches per minute, with the first two inches of test measurements providing static COF and the remaining measuring kinetic COF. Results are reported as the average of three tests on the same sample.

When delivered from a solvent and applied to aluminum panels, the silsesquioxane resin wax gave slip as seen by the CoF which can relate to low transfer and anti-blocking. In addition, the contact angle and CoF varies and can be manipulated based on the composition of the silsesquioxane resin wax. When applied to vinyl substrates, the effect can be a non-tacky matte finish with a nice feel. This property can be advantageous in some automotive vinyl treatments. These properties could also be delivered when the silsesquioxane resin wax is used as an additive in a surface coating.

Example 14

Wax Deposition Inhibition in Crude Oil

Crude oil used: Medium Gravity GOM (Gulf of Mexico) Crude

Testing: Standard cold-finger test. Oil at 105° F. with a $\Delta T$ of 15° F.

TABLE 19

Cold Finger Test Results

| Material | Dose (ppm) | % Inhibition compared to blank without the additive | Comments |
|---|---|---|---|
| 2-1, C30+ | 150 | 61.9 | Deposit thinner than blank |
| 2-1, C30+ | 112 | 51.7 | Deposit thinner than blank |
| 1-2, C30+ | 147 | 3.3 | Soft deposit, some bare probe as compared to blank |
| 1-3, C30+ | 150 | 62.0 | Majority bare probe |
| 1-3, C30+ | 111 | 41.9 | ~50% bare probe |

Cold-Finger Testing Procedure:

The basis of this test is to measure the amount of wax deposited on a cold surface while maintaining the oil at a temperature above the cloud point. The oil temperature is maintained by immersion of the oil container in an isothermal bath. The cold surface is a probe with circulating fluid inside it (the cold finger). Once the oil is at the desired test temperature, the cold finger is lowered into the oil container. After a fixed period of time, the probe is removed from the oil and the amount of wax deposited on the probe is measured. In this example, the oil temperature is 105° F. and the cold finger is 15° F. cooler (delta T=15° F.). The % inhibition is as compared to a blank, where 0%=no inhibition and 100% no wax deposition.

By way of this example, it is demonstrated that the use of the silsesquioxane resin wax can reduce the amount of wax deposition, as well as change the character of any wax deposited, which may ease removal.

The invention claimed is:

1. A silsesquioxane resin wax comprising at least 40 mole % of siloxy units having the formula $(R_2R'SiO_{1/2})_x(R"SiO_{3/2})_y$, where x and y have a value of 0.05 to 0.95 and a certain y/x ratio, R is an alkyl group having from 1 to 8 carbon atoms, an aryl group, a carbinol group, or an amino group, R' is a monovalent hydrocarbon having 18-40 carbon atoms, and R" is a monovalent hydrocarbon group having 1 to 8 carbon atoms or an aryl group, provided R' and the y/x ratio are selected such that the silsesquioxane wax has a melting point greater than 30° C.

2. The composition of claim 1 wherein the silsesquioxane resin wax comprises the units:
   (i) $(R^1_3SiO_{1/2})_a$
   (ii) $(R^2_2SiO_{2/2})_b$
   (iii) $(R^3SiO_{3/2})_c$,
   (iv) $(SiO_{4/2})_d$,
   (v) $(R_2R'SiO_{1/2})_x$ and
   (vi) $(R"SiO_{3/2})_y$,
   wherein
   R, $R^1$, $R^2$, and $R^3$ are independently an alkyl group having from 1 to 8 carbon atoms, an aryl group, a carbinol group, or an amino group,
   R' is a monovalent hydrocarbon having 9-40 carbon atoms,
   R" is a monovalent hydrocarbon group having 1 to 8 carbon atoms or an aryl group
   a, b, c, and d have value of zero to 0.4,
   x and y have a value of 0.05 to 0.95,
   with the provisos that the value of x+y is equal to or greater than 0.40,
   and the value of a+b+c+d+x+y=1.

3. The silsesquioxane resin wax of claim 1 further comprising;
   (C) a carrier selected from a volatile siloxane or organic solvent.

4. A personal care product comprising the silsesquioxane resin wax of claim 1.

5. The personal care product of claim 4, where the personal care product is a moisturizing cream or lotion.

6. A household care product comprising the silsesquioxane resin wax of claim 1.

7. A crude oil wax control product comprising the silsesquioxane resin wax of claim 1.

8. An automotive care product comprising the silsesquioxane resin wax of claim 1.

9. A process for preparing a silsesquioxane resin wax comprising reacting;
   A) a SiH containing alkyl silsesquioxane resin comprising siloxy units of the formula $(R_2HSiO_{1/2})_x(R"SiO_{3/2})_y$, where R is an alkyl group having from 1 to 8 carbon atoms, an aryl group, a carbinol group, or an amino group, R" is a monovalent hydrocarbon group having 1 to 8 carbon atoms or an aryl group, x and y have a value of 0.05 to 0.95 and a certain ratio, with the provisos that the value of x+y in the SiH containing alkyl, silsesquioxane resin is equal to or greater than 0.40,
   B) a $C_{18}$-$C_{40}$ vinyl terminated hydrocarbon,
   C) a hydrosilylation catalyst, and optionally
   D) a solvent,
   provided the $C_{18}$-$C_{40}$ vinyl terminated hydrocarbon and the y/x ratio are selected such that the silsesquioxane wax has a melting point greater than 30° C.

10. A personal care product comprising the silsesquioxane resin wax of claim 3.

11. A household care product comprising the silsesquioxane resin wax of claim 3.

12. A crude oil wax control product comprising the silsesquioxane resin wax of claim 3.

13. An automotive care product comprising the silsesquioxane resin wax of claim 3.

* * * * *